United States Patent
Lee et al.

(10) Patent No.: US 10,828,402 B2
(45) Date of Patent: Nov. 10, 2020

(54) COLLAR CONNECTOR

(75) Inventors: Eric Lee, Irvine, CA (US); Robert Balsamo, Lake Forest, CA (US)

(73) Assignee: Alcon Inc., Fribourg (CH)

( * ) Notice: Subject to any disclaimer, the term of this patent is extended or adjusted under 35 U.S.C. 154(b) by 1613 days.

(21) Appl. No.: 13/273,288

(22) Filed: Oct. 14, 2011

(65) Prior Publication Data

US 2013/0092247 A1    Apr. 18, 2013

(51) Int. Cl.
*A61M 1/00* (2006.01)
*A61M 39/10* (2006.01)

(52) U.S. Cl.
CPC ........ *A61M 1/0064* (2013.01); *A61M 39/105* (2013.01); *A61M 2039/1027* (2013.01); *A61M 2039/1066* (2013.01); *A61M 2039/1077* (2013.01); *A61M 2039/1094* (2013.01); *Y10T 137/0402* (2015.04)

(58) Field of Classification Search
CPC .............. A61M 1/0064; A61M 39/105; A61M 2039/1077; A61M 2039/1094; A61M 2039/1066; A61M 2039/1027
USPC .......... 285/124.1, 124.2, 124.3, 124.4, 124.5
See application file for complete search history.

(56) References Cited

U.S. PATENT DOCUMENTS

| | | | |
|---|---|---|---|
| 4,652,255 A | 3/1987 | Martinez | |
| 4,900,271 A | 2/1990 | Colleran et al. | |
| 4,904,238 A | 2/1990 | Williams | |
| 4,921,477 A | 5/1990 | Davis | |
| 4,953,929 A | 9/1990 | Basista et al. | |
| 5,073,042 A | 12/1991 | Mulholland et al. | |
| 5,219,185 A * | 6/1993 | Oddenino | 285/26 |
| 5,343,547 A | 8/1994 | Palecek et al. | |
| 5,501,840 A * | 3/1996 | Mantovani | A61M 39/08 138/111 |

(Continued)

FOREIGN PATENT DOCUMENTS

| | | |
|---|---|---|
| DE | 19854485 A1 | 5/2000 |
| JP | H0561266 B | 9/1993 |

(Continued)

OTHER PUBLICATIONS

European Patent Office, European Search Report, Application No. 12840545.3, dated Jun. 25, 2014, 6 pages.

(Continued)

*Primary Examiner* — James M Hewitt, II

(57) ABSTRACT

In various embodiments, a connector system may include at least two connectors and a collar configured to detachably align the at least two connectors for coupling to a mating collar with at least two mating connectors. The collar may also be configured to at least partially disengage from the at least two connectors to allow movement of the connectors relative to each other. The relative movement may allow the connectors to couple to mating connectors that are in different configurations (than the mating collar configurations). In some embodiments, the connectors and/or mating connectors may include complementary male/female connectors. In some embodiments, the collar/mating collar may circumscribe their respective connectors and/or a perimeter of the other of the collar/mating collar. In some embodiments, the collar/mating collar may include interfacing features.

14 Claims, 8 Drawing Sheets

(56) References Cited

U.S. PATENT DOCUMENTS

| | | | |
|---|---|---|---|
| 5,533,996 A * | 7/1996 | Murphey | A61M 39/14 |
| | | | 604/535 |
| 5,681,063 A | 10/1997 | Bressner | |
| 6,062,244 A * | 5/2000 | Arkans | 137/1 |
| 6,149,622 A | 11/2000 | Marie | |
| 7,500,790 B2 | 3/2009 | Erdman et al. | |
| 2005/0184264 A1 | 8/2005 | Tesluk | |
| 2006/0153634 A1 | 7/2006 | Jensen et al. | |
| 2006/0260699 A1 * | 11/2006 | Edelman | A61M 39/1011 |
| | | | 137/614.04 |
| 2007/0032776 A1 | 2/2007 | Miyahara | |
| 2007/0260173 A1 | 11/2007 | Boukhny et al. | |
| 2008/0154282 A1 | 6/2008 | Faught et al. | |
| 2008/0275429 A1 * | 11/2008 | Sage | A61M 25/0014 |
| | | | 604/536 |
| 2010/0283238 A1 * | 11/2010 | Deighan | A61M 39/10 |
| | | | 285/328 |
| 2011/0105999 A1 | 5/2011 | Akahoshi | |
| 2011/0270230 A1 * | 11/2011 | Sage | A61M 39/12 |
| | | | 604/533 |
| 2012/0004655 A1 | 1/2012 | Kim et al. | |

FOREIGN PATENT DOCUMENTS

| | | |
|---|---|---|
| WO | 97/48426 A2 | 12/1997 |
| WO | 97/48426 A3 | 3/1998 |
| WO | 2004/037339 A1 | 5/2004 |
| WO | 2010/127461 A1 | 11/2010 |
| WO | 2013055580 A1 | 4/2013 |

OTHER PUBLICATIONS

International Searching Authority, International Search Report, PCT/US2012/058869, dated Jan. 4, 2013, 2 pages.

International Searching Authority, Written Opinion of the International Searching Authority, PCT/US2012/058869, dated Jan. 4, 2013, 6 pages.

* cited by examiner

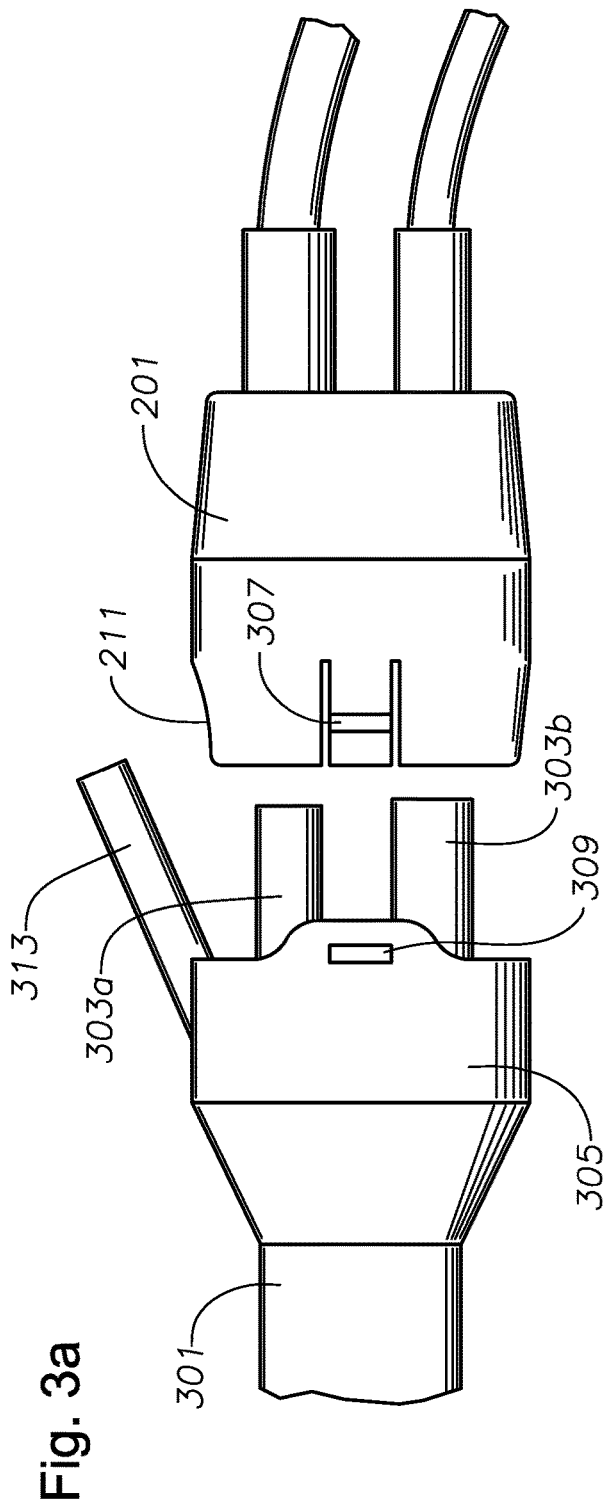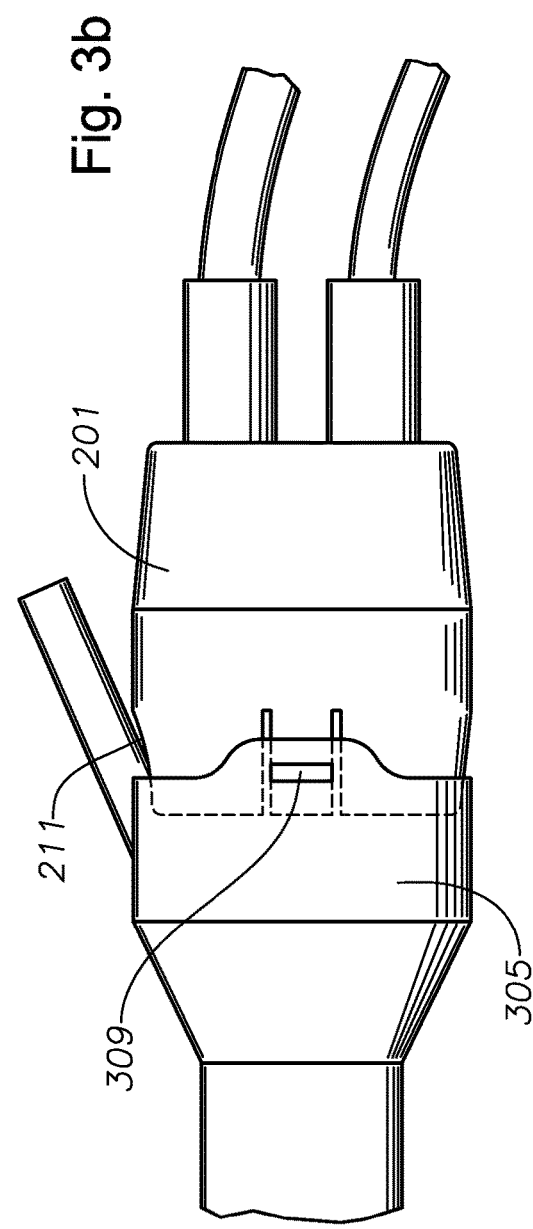

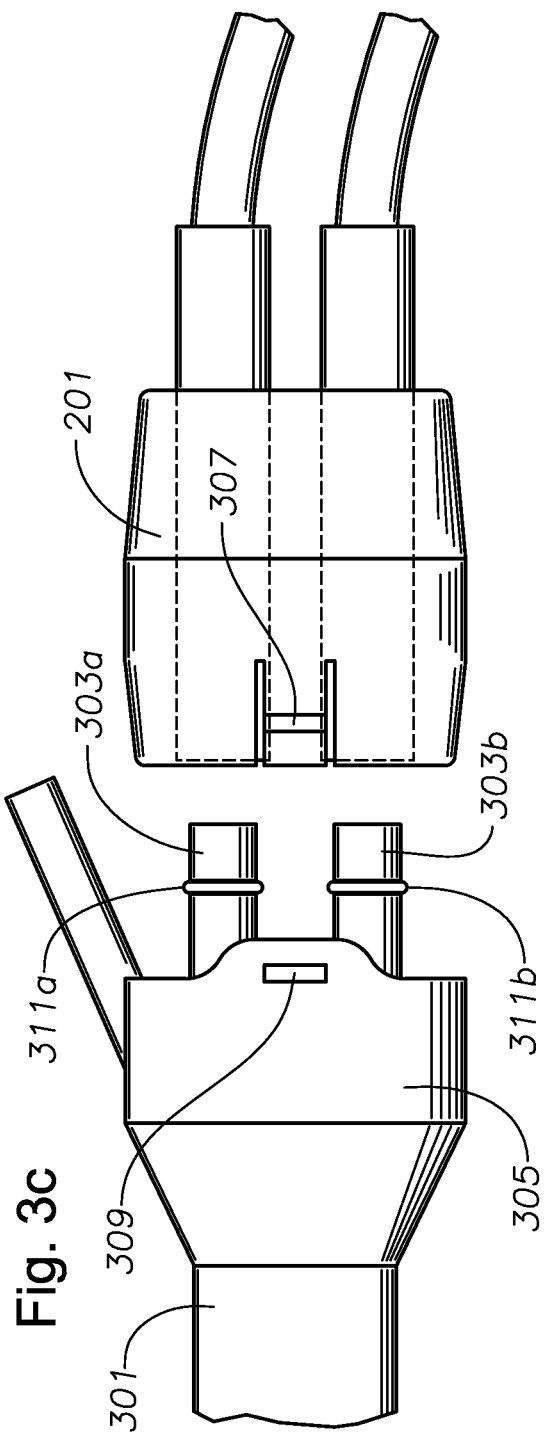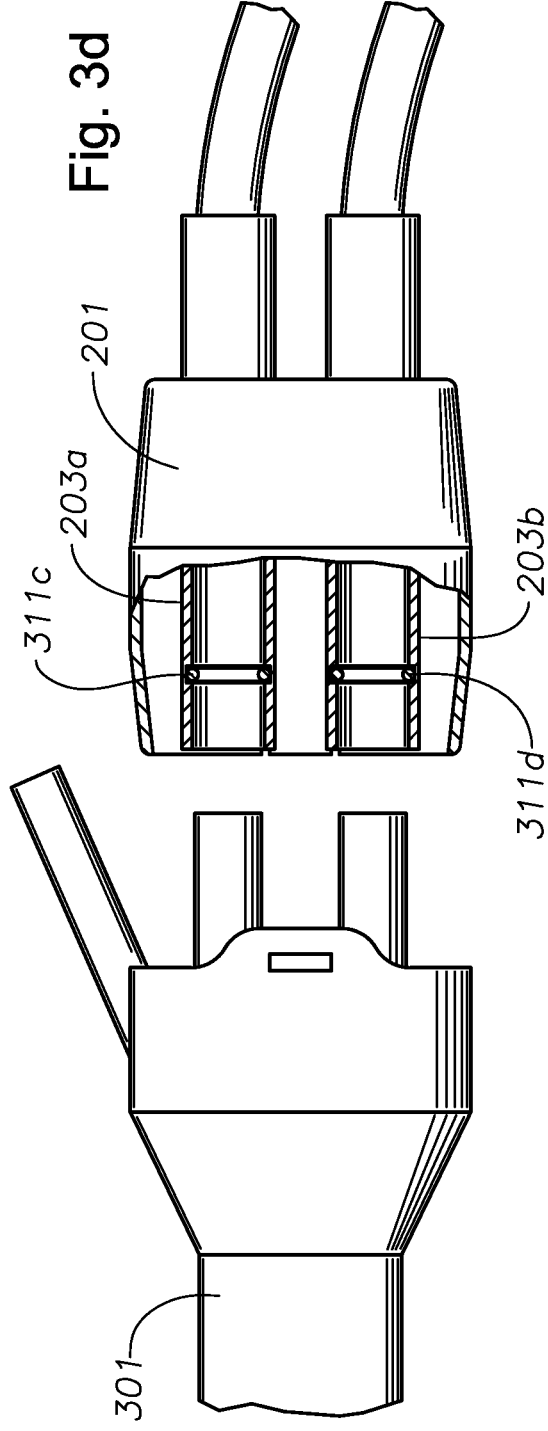

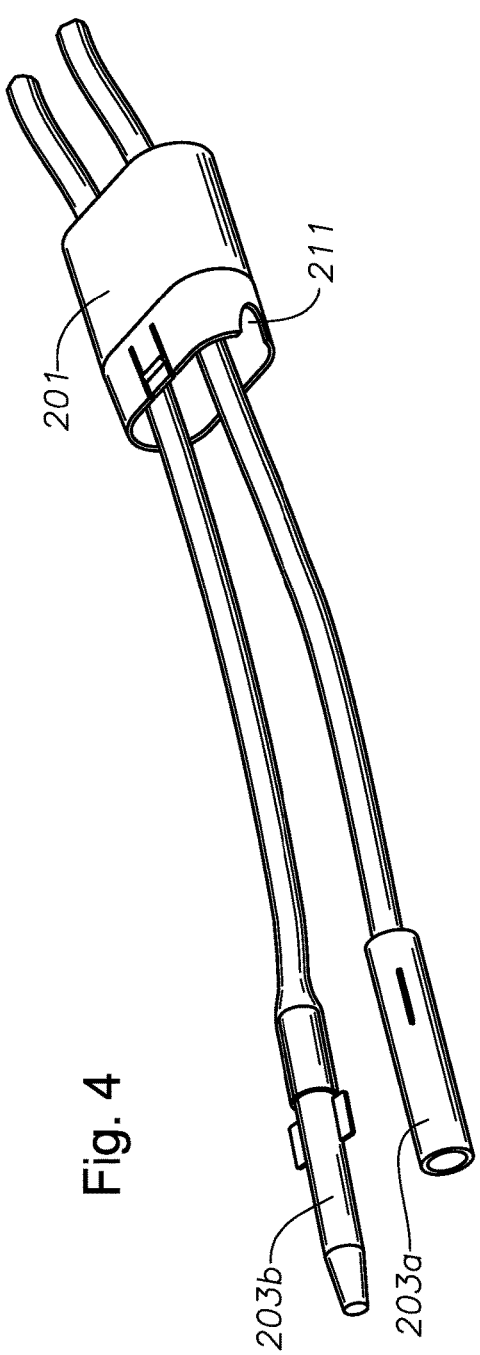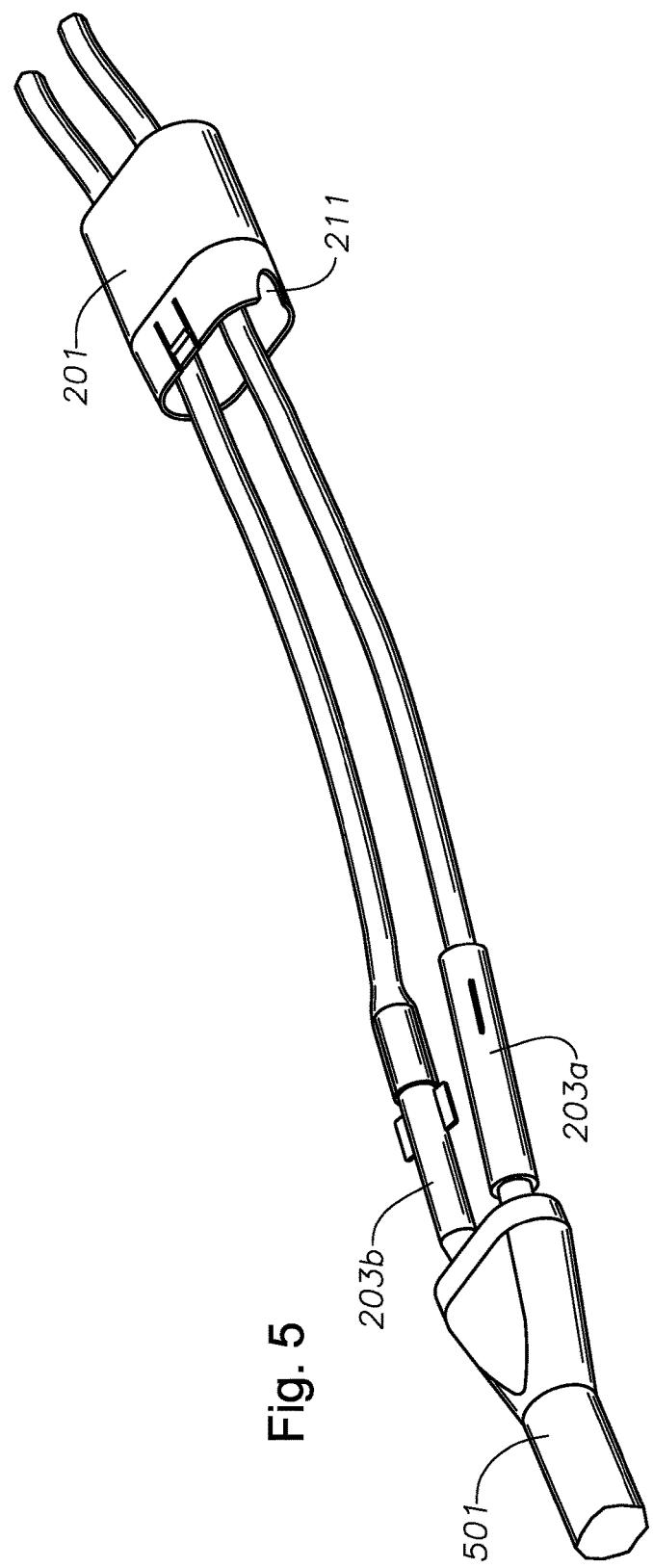

COLLAR CONNECTOR

FIELD OF THE INVENTION

The present invention generally pertains to connectors. More particularly, but not by way of limitation, the present invention pertains to a convertible collar for multiple connectors.

DESCRIPTION OF THE RELATED ART

Devices, such as handpieces, may use multiple connectors. For example, as seen in FIG. 1 a prior art ophthalmic handpiece may connect to multiple lines (e.g., aspiration line, irrigation line, power line, etc.) through different connectors on the handpiece. The respective lines may include separate connectors that are configured to be received in the respective connectors of the handpiece.

SUMMARY

In various embodiments, a connector system may include at least two connectors and a collar configured to detachably align the at least two connectors for coupling to a mating collar with at least two mating connectors. The collar may also be configured to at least partially disengage from the at least two connectors to allow movement of the connectors relative to each other. The relative movement may allow the connectors to couple to mating connectors that are in different configurations (than the mating collar configurations). In some embodiments, the connectors may couple lines (such as tubing, cables, etc.) from sources of irrigation, aspiration, power, etc. in a surgical console to mating connectors (e.g., irrigation/aspiration connectors on a handpiece). In some embodiments, the connectors and/or mating connectors may include complementary male/female connectors (other types of connectors are also contemplated). In some embodiments, the collar/mating collar may circumscribe their respective connectors and may further be configured to circumscribe a perimeter of the other of the collar/mating collar when the collar and mating collar are coupled together. In some embodiments, the collar/mating collar may include features and complementary features configured to interact to further secure the collar and mating collar together.

BRIEF DESCRIPTION OF THE DRAWINGS

For a more complete understanding of the present invention, reference is made to the following description taken in conjunction with the accompanying drawings in which:

FIGS. 3a-d illustrate an interface between the collar and a mating collar, according to an embodiment;

FIG. 4 illustrates a view of the collar disengaged from the connectors, according to an embodiment;

FIG. 5 illustrates the separated fluid lines connected to a handpiece, according to an embodiment;

It is to be understood that both the foregoing general description and the following detailed description are exemplary and explanatory only and are intended to provide a further explanation of the present invention as claimed.

DETAILED DESCRIPTION OF THE EMBODIMENTS

Figure 1:
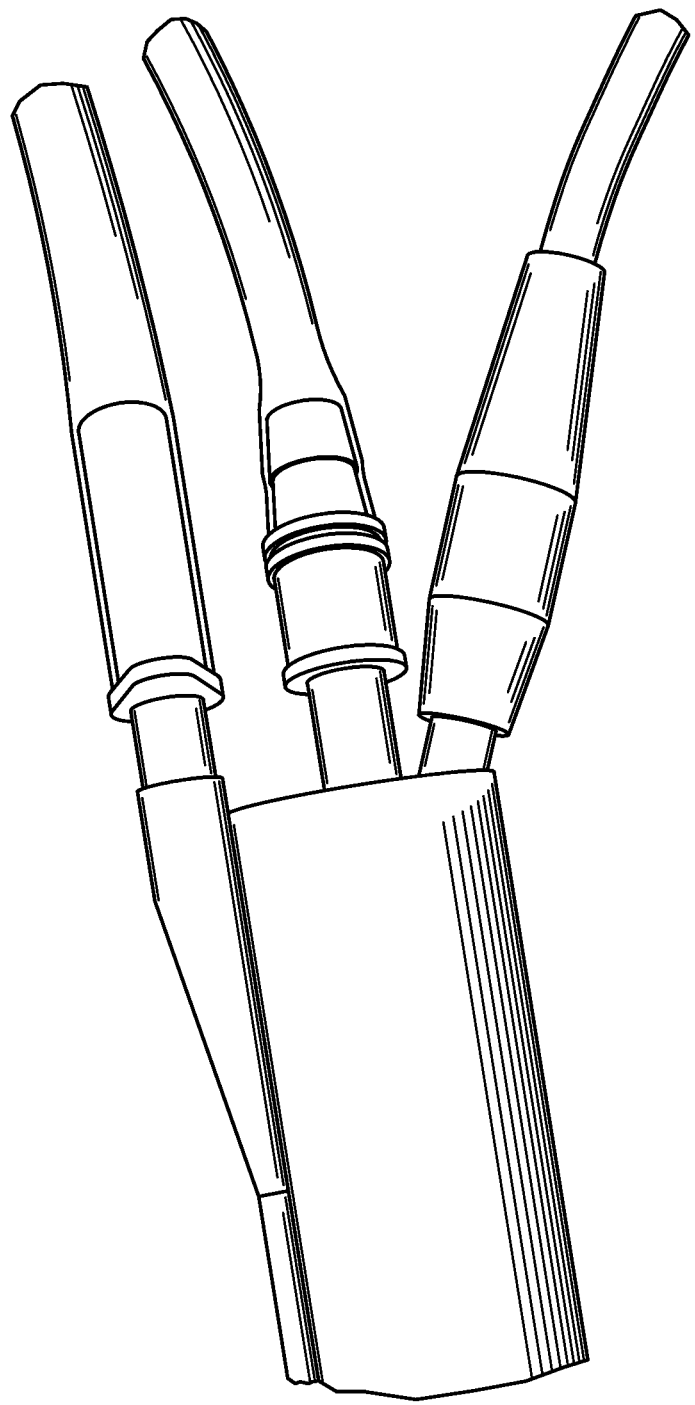
FIG. 1 illustrates a prior art figure showing multiple single connectors in a handpiece.
Figure 2A:
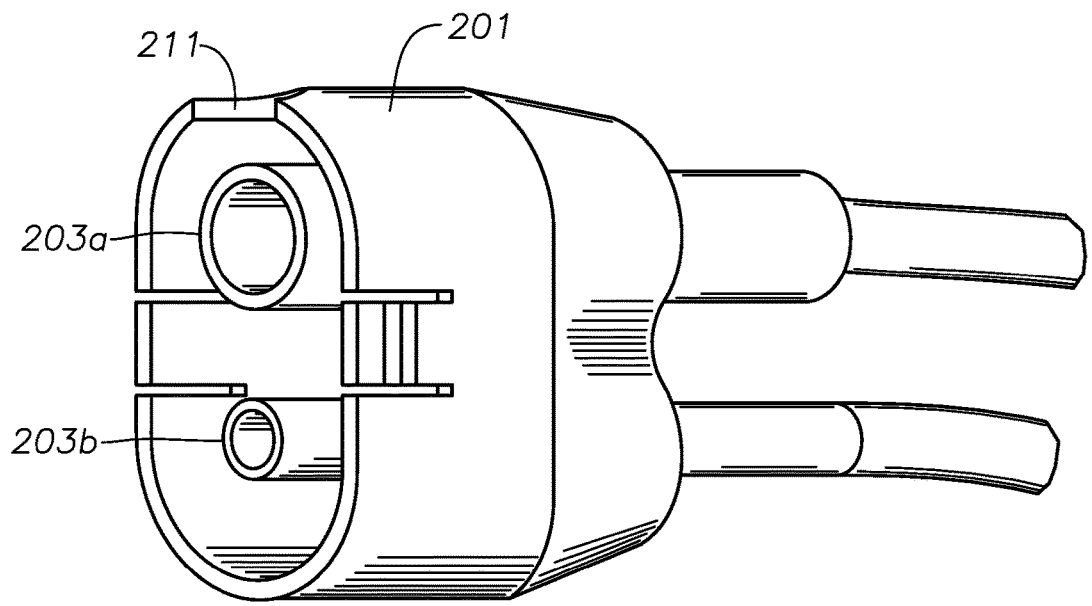
FIGS. 2a-c illustrate a collar for aligning at least two connectors, according to an embodiment.
Figure 2B:
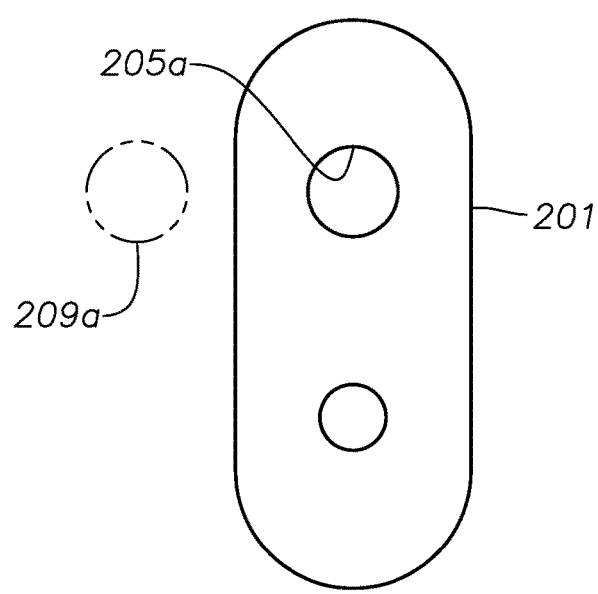
Figure 2C:
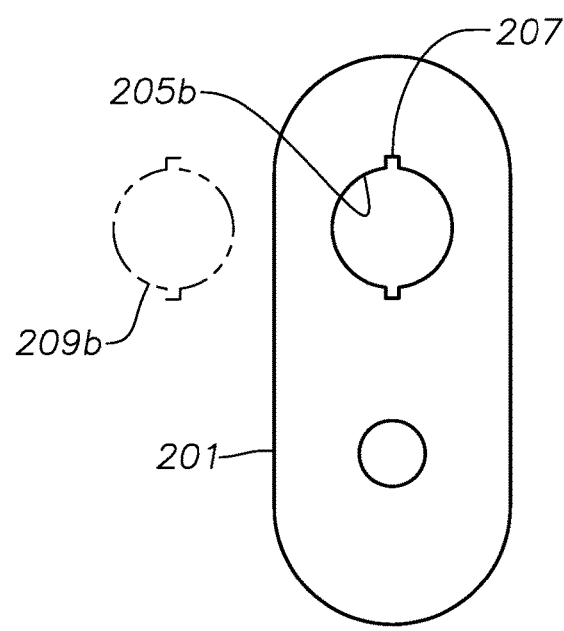

FIGS. 2a-c illustrate a collar 201 for aligning at least two connectors 203, according to an embodiment. In some embodiments, collar 201 may align first connector 203a and second connector 203b. As part of the alignment, the collar 201 may couple the connectors 203 relative to each other to facilitate connection between the connectors 203 and mating connectors (e.g., as seen in FIG. 3a). The connectors 203 and collar 201 may be made of plastic, metal, etc. Aligning the connectors 203 in the collar 201 may include inserting the connectors 203 through apertures in the collar 201 that are sized to receive an outer casing of the connectors 203. For example, the connector casings may have tapered profiles and at least a portion of the tapered profiles may have a diameter that is smaller than a respective collar aperture (e.g., aperture 205a as shown in FIG. 2b which illustrates a back end of the collar 201 and a cross section of corresponding connector casing 209a) while a portion of the tapered casing may have a diameter that is larger than the respective collared aperture 205a such that as the tapered casing is received in the collar aperture 205a, the casing slides until a friction fit is formed between the portion of the tapered casing with the larger diameter than the collar aperture 205a. As seen in FIG. 2c, the collar aperture 205b may include a feature (e.g., feature 207) that may engage and/or secure a complementary feature on the connector casing 209b (e.g., the cutout feature 207 may engage a projecting feature on the connector casing 209b (shown in cross-section) to secure the connector casing 209b to the collar 201). Other fastening mechanisms between the connectors 203 and collar 201 are also contemplated (e.g., snap fittings, twist and lock fitting, etc). In some embodiments, the connectors 203 may be permanently coupled in the collar 201 (e.g., through adhesive, a melted interface, etc).

FIGS. 3a-c illustrate an interface between the collar 201 and a mating collar 305, according to an embodiment. The aligned connectors 203 may be configured to interface with mating connectors 303 (e.g., connectors 303a,b). The mating connectors 303 may be aligned through a mating collar 305. In some embodiments, the mating collar 305 may be formed as part of a connected device (e.g., formed as part of an outer device casing) or the mating collar 305 may be separate from the connected device. In some embodiments, connector 203a may be a female connector configured to receive male connector 303a. In some embodiments, connector 203b may be a male connector configured to be received in female connector 303b. Other connector configurations are also contemplated (e.g., connector 203b may be a female connector, both connectors 203 may be male connectors, etc). Other connector types are also contemplated (e.g., snap connections, welded connections, magnetic connections, etc). While two connectors 203 are shown with two mating connectors 303, other numbers of connectors are also contemplated (e.g., 3, 5, 10, 100, etc).

In some embodiments, the connectors 203 may couple to lines from sources of irrigation, aspiration, pneumatics, power, etc. (e.g., from a surgical console such as an ophthalmic surgical console configured for cataract/retina procedures). The lines may include tubing, cables, etc. In some embodiments, the mating connectors 303 may be handpiece connectors coupled to various handpiece functions (e.g., aspiration, irrigation, power, etc). In some embodiments, the collar 201 may have a particular configuration to interface with a particular mating collar 305. For example, a particular fit between the collar 201 and mating collar 305 may prevent the collar 201 and connectors 203 from being improperly used with incorrect handpieces (e.g., prevent a collar with irrigation/aspiration lines from being plugged into a pneumatic handpiece). The particular fit may also insure that the connector 203a for irrigation is properly connected to the corresponding mating irrigation connector 303 (and that the connector 203b for aspiration is properly connected to the corresponding mating aspiration connector 303). The collar 201/mating collar 305 system may also allow for the connection of multiple connectors in a "one-step" connection process (i.e., the step of connecting the collar 201 to the mating collar 305 may connect their respective connectors). In some embodiments, the collar 201 and mating collar 305 may not couple if they are incorrectly oriented (e.g., if the collar 201 is flipped and, for example, an irrigation connector 203a is aligned with an aspiration connector 303b of the handpiece 301). In some embodiments, the collar 201 may include a recess 211 to allow for branched connector 313. This may further insure the collars 201/305 are correctly aligned (i.e., the connector 313 may interfere with a proper fit if collar 201 is flipped and recess 211 is not aligned with the connector 313).

In some embodiments, the mating collar 305 may circumscribe the connectors 303a,b and may be configured to circumscribe a perimeter of the collar 201 when the collar 201 is received in the mating collar 305 (e.g., during coupling of the connectors 203a,b to the connectors 303a,b). In some embodiments, the mating collar 305 may be received in the collar 201 (e.g., the collar 201 may be configured to circumscribe a perimeter of the mating collar 305). In some embodiments, the engaged perimeters of the collar 201 and mating collar 305 (e.g., see FIG. 3b) may form a seal to protect the connections formed between the connectors 203a,b and the connectors 303a,b. In some embodiments, the collar 201 and/or mating collar 305 may not circumscribe their respective connectors. For example, the collar 201 and the mating collar 305 may abut each other without extending over each other.

In some embodiments, the collar 201 may include a feature configured to couple to a complementary feature of the mating collar 305. For example, at least one of the feature and complementary feature may include a projection (e.g., projection 307) and the other of the feature and complementary feature may include an aperture (e.g., aperture 309) for receiving the projection 307. The feature/complementary feature coupling between the collar 201 and mating collar 305 may increase the grip between the collar 201 and mating collar 305 when they are engaged. The grip between the collar 201 and mating collar 305 may further secure the connections between the connectors 203 and mating connectors 303 when the collar 201 and mating collar 305 are engaged. The collar 201/mating collar 305 system may also facilitate proper insertion pressure between the connectors 203a,b and connectors 303a,b. For example, when the collar 201 is properly mated to the mating collar 305, the connections between the connectors 203a,b and connectors 303a,b may be at a predetermined insertion force/spacing (determined with respect to the collar/mating collar structure). For example, if the connectors 203a,b and connectors 303a,b seal through a friction fit, a connection that is too loose may result in leaking while a connection that is too tight may make the connectors difficult to separate. The collar 201/mating collar 305 interface may connect the connectors with enough force to prevent leaking and allow separation when needed. In some embodiments, as seen in FIG. 3c, one or more o-rings may be used between the connectors. For example, o-ring 311a,b may be fitted on respective connectors 303a,b such that when the connectors 303a,b are received in connectors 203a,b a seal is formed between the outer surface of the o-rings 311a,b and the inner surface of connectors 203a,b. In some embodiments, the o-rings may be located in the interior of connectors 203a,b (e.g., as seen in FIG. 3d, the o-rings may be placed inside the receiving connectors 203a,b to form a seal between the connectors 203a,b and 303a,b (when connectors 303a,b are received inside connectors 203a,b). In some embodiments, one of the connectors 203a,b may be a male connector and the other connector may be a female connector (to fit with corresponding connectors 303a,b) to further insure correct alignment of the connectors (the o-rings may be placed inside the receiving female connectors of the 203a,b and 303a,b connectors).

FIG. 4 illustrates a view of the collar 201 disengaged from the connectors 203, according to an embodiment. For example, the collar 201 may be pulled back from the connectors 203 to allow the connectors 203 to separate for connecting to mating connectors in a different configuration (than, for example, the mating connectors of FIG. 3). This may allow, for example, irrigation/aspiration connectors to be used with an irrigation/aspiration handpiece having irrigation/aspiration connectors in a different configuration. Requiring the user to disengage the collar 201 to individually attach the connectors 203 may serve as an indication to the user that special care needs to be exercised to make sure the connectors 203 are being properly used with the handpiece having connectors 203 in a different configuration (e.g., to make sure the handpiece is properly configured to work with the console in the current irrigation/aspiration setup).

FIG. 5 illustrates the separated connectors 203 connected to a handpiece 501, according to an embodiment. The collar 201 may be disengaged from the connectors 203 to allow the connectors to connect to mating connectors on handpiece 501 that are oriented/angled in different configurations than the mating connectors 303 configured for mating with the connectors 203 when aligned by collar 201.

Figure 6A:
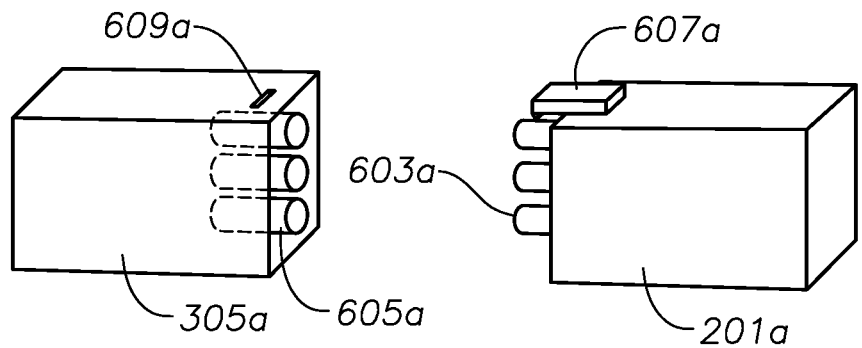
FIGS. 6a-c illustrate various embodiments of the collar/mating collar.
Figure 6B:
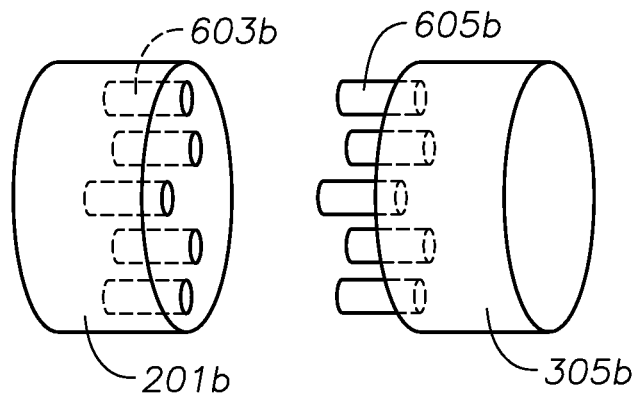
Figure 6C:
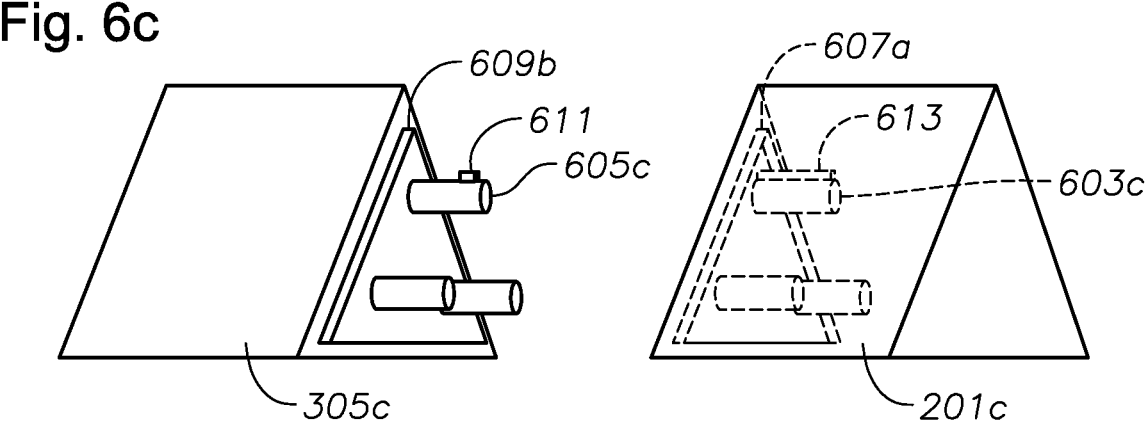

FIGS. 6a-c illustrate embodiments of the collar 201 and mating collar 305. As seen in FIG. 6a, collar 201a may include feature 607a (e.g., a projection extended from a flexible latch) and a complementary feature 609a shaped to receive the projection. Connectors 603a may be configured to be received in mating connectors 605a. As seen in FIG. 6b, connectors 603b may be configured to receive mating connectors 605b. In some embodiments, a friction fit between the connectors and mating connectors may be sufficient to hold the collar 201 and mating collar 305 together (e.g., there may not be a feature/complementary feature to further secure the collar and mating collar together). As seen in FIG. 6c, connectors 603c may receive mating connectors 605c. The feature 609b may include a projected part that is configured to be received in complementary recess feature 607a for insuring proper orientation and/or to provide a friction fit to further secure the collar 201c and mating collar 305c. In some embodiments, the collars 201 may have a particular configuration to interface with a particular mating collar 305. For example, a particular fit between the collar 201 and mating collar 305 may prevent the collar 201 and connectors 203 from being improperly used with incorrect handpieces (e.g., prevent a collar with irrigation/aspiration lines from being plugged into a pneumatic handpiece). In some embodiments, a connector may include a keyed feature 611 to fit inside a receiving feature 613 to insure correct alignment of the connectors (other feature/receiving feature configurations are also contemplated).

Figure 7:
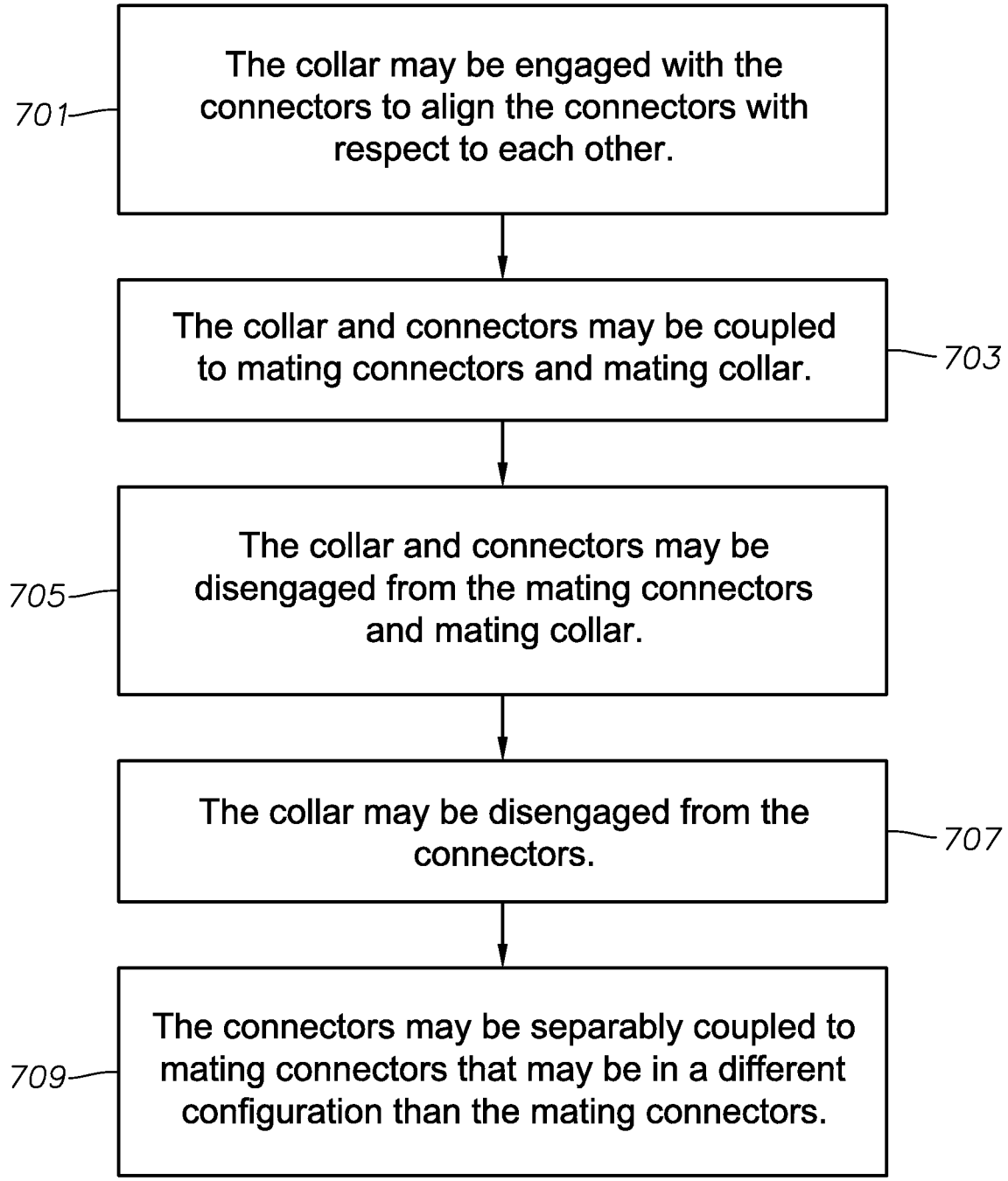
FIG. 7 illustrates a flowchart of a method for assembling the collared connection, according to an embodiment.

FIG. 7 illustrates a flowchart of a method for assembling the collared connection, according to an embodiment. The elements provided in the flowchart are illustrative only. Various provided elements may be omitted, additional elements may be added, and/or various elements may be performed in a different order than provided below.

At 701, collar 201 may be engaged with connectors 203 to align connectors 203 with respect to each other.

At 703, the collar 201 and connectors 203 may be coupled to mating connectors 303 and mating collar 305.

At 705, the collar 201 and connectors 203 may be disengaged from the mating connectors 303 and mating collar 305.

At 707, the collar 201 may be disengaged from the connectors 203.

At 709, the connectors 203 may be separably coupled to mating connectors that may be in a different configuration than the mating connectors 303.

Figure 8:
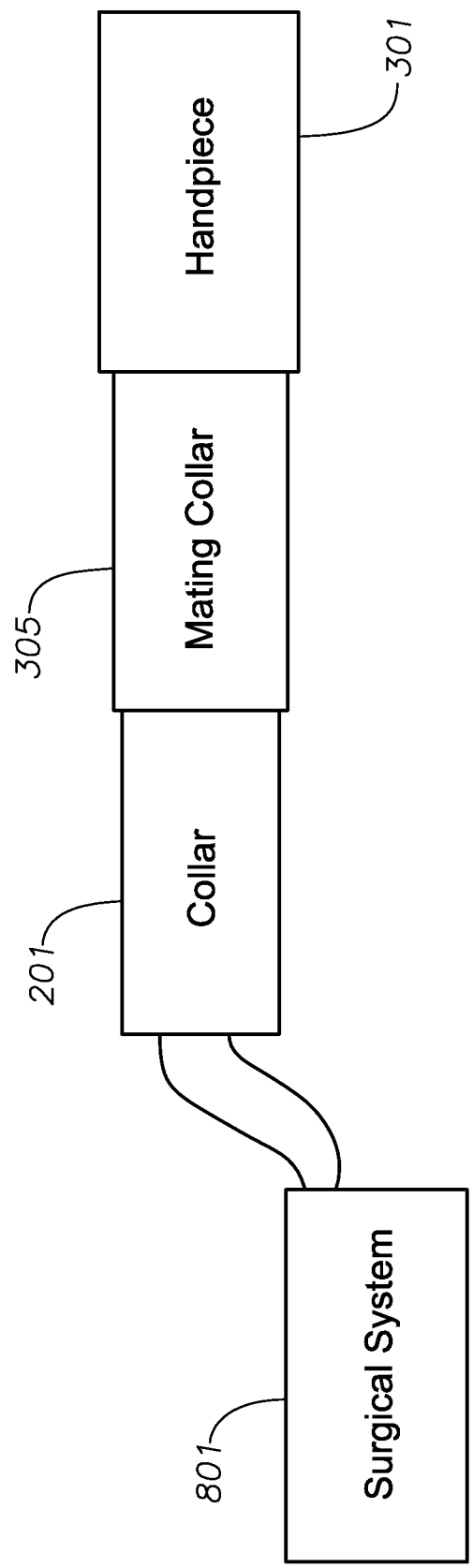
FIG. 8 illustrates a surgical console coupled to a handpiece through the collar/mating collar connection, according to an embodiment.

FIG. 8 illustrates a surgical console coupled to a handpiece through the collar/mating collar connection, according to an embodiment. As seen in FIG. 8, surgical console 801 may be coupled to an irrigation/aspiration handpiece 301 through the collar 201/mating collar 305 connection. Other console/handpiece types are also contemplated.

Various modifications may be made to the presented embodiments by a person of ordinary skill in the art. Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. An apparatus, comprising:
   a first connector coupled to a first tube;
   a second connector coupled to a second tube;
   a collar comprising a first aperture and a second aperture, wherein, in a first state, the first aperture and second aperture align the first connector and the second connector, respectively, for coupling to an aligned third connector and fourth connector;
   wherein in a second state, the first aperture and second aperture of the collar are disengaged from the first connector and second connector, respectively, to allow movement of the first connector relative to the second connector, wherein, in the second state, the first aperture slides along the first tube and the second aperture slides along the second tube;
   wherein the first connector is secured to the collar, in the first state, through a releasable friction fit with the first aperture and wherein the first connector is detached from the collar, in the second state, by pulling back the collar over the first tube to overcome the friction fit between the first connector and the first aperture of the collar;
   wherein the apparatus transitions from the second state to the first state by pulling the collar back over the first connector and second connector to reestablish the friction fit between the first connector and the first aperture of the collar and reestablish the friction fit between the second connector and the second aperture of the collar.

2. The apparatus of claim 1, wherein, in the first state, the collar engages a mating collar, wherein the mating collar aligns the third and fourth connector.

3. The apparatus of claim 2, wherein the mating collar circumscribes the third and fourth connector and wherein the mating collar circumscribes a perimeter of the collar when the collar is received in the mating collar.

4. The apparatus of claim 2, wherein the collar circumscribes the first and second connector and wherein the collar circumscribes a perimeter of the mating collar when the mating collar is received in the collar.

5. The apparatus of claim 3, wherein the mating collar is comprised in an aspiration/irrigation handpiece and wherein the third connector and fourth connector are irrigation and aspiration connectors, respectively.

6. The apparatus of claim 2, wherein the collar comprises an engagement feature and wherein the mating collar comprises a complementary engagement feature coupling the collar engagement feature.

7. The apparatus of claim 6, wherein at least one of the engagement feature and complementary engagement feature comprises a projection and wherein the other of the engagement feature and complementary engagement feature comprises an aperture for receiving the projection.

8. The apparatus of claim 1, wherein at least one of the first connector and the second connector is a male connector and wherein at least one of the third connector and the fourth connector is a female connector receiving the at least one male first or second connector.

9. The apparatus of claim 1,
   wherein the first connector is accessible through a first end of the collar and wherein the first tube enters the collar through an opposing second end of the collar;
   wherein as the first connector is pulled through the first end of the collar, the first tube is pulled into the second end of the collar.

10. The apparatus of claim 9, wherein the first connector includes a feature that engages with a complementary feature on the collar when the first connector engages the collar to secure the first connector to the collar.

11. The apparatus of claim 9, wherein, to transition the apparatus from the second state to the first state, the first connector is pulled back into and secured to the collar after previously being pulled away from the collar.

12. The apparatus of claim 9, wherein the first connector is detachably coupled to the collar through a snap fitting.

13. The apparatus of claim 9, wherein the first connector is detachably coupled to the collar through a twist and lock fitting.

14. The apparatus of claim 1,
   wherein, in the second state, when the collar is disengaged from the first and second connectors, the collar circumscribes a portion of the first tubing and circumscribes a portion of the second tubing, and
   wherein, in the second state, when the collar is disengaged from the first and second connectors, the first connector is still coupled to the first tubing, and the second connector is still coupled to the second tubing.

* * * * *